United States Patent
Kopelman et al.

(10) Patent No.: US 7,393,208 B2
(45) Date of Patent: **\*Jul. 1, 2008**

(54) METHOD AND SYSTEM FOR ASSISTING IN APPLYING AN ORTHODONTIC TREATMENT

(75) Inventors: Avi Kopelman, Ramat Chen (IL); Eldad Taub, Reut (IL); Baruch Nissenbaum, Ramat Gan (IL)

(73) Assignee: Cadent Ltd., Or Yehuda (IL)

( \* ) Notice: Subject to any disclaimer, the term of this patent is extended or adjusted under 35 U.S.C. 154(b) by 0 days.

This patent is subject to a terminal disclaimer.

(21) Appl. No.: 10/797,126

(22) Filed: Mar. 11, 2004

(65) Prior Publication Data

US 2004/0175670 A1    Sep. 9, 2004

Related U.S. Application Data

(63) Continuation of application No. 10/059,728, filed on Jan. 29, 2002, now abandoned.

(51) Int. Cl.
*A61C 3/00* (2006.01)
(52) U.S. Cl. ......................................... 433/24
(58) Field of Classification Search ................... 433/24, 433/213
See application file for complete search history.

(56) References Cited

U.S. PATENT DOCUMENTS

| | | | | |
|---|---|---|---|---|
| 4,850,864 A | \* | 7/1989 | Diamond | 433/3 |
| 5,879,158 A | | 3/1999 | Doyle et al. | 433/24 |
| 6,061,004 A | \* | 5/2000 | Rosenberg | 341/20 |
| 6,152,731 A | | 11/2000 | Jordan et al. | 433/69 |
| 6,227,850 B1 | | 5/2001 | Chishti et al. | 433/24 |
| 6,318,995 B1 | | 11/2001 | Sachdeva et al. | 433/24 |

(Continued)

FOREIGN PATENT DOCUMENTS

FR    2656215 A1 \* 6/1991

(Continued)

OTHER PUBLICATIONS

Lawrence, A.F.; *Straight Wire The Concept and Appliance*, pp. 13-24, (1989), L.A. Wells Co., CA, US.

(Continued)

*Primary Examiner*—John J Wilson
(74) *Attorney, Agent, or Firm*—The Nath Law Group; Jerald L. Meyer; Matthew J. Moffa (57) ABSTRACT

A method and system for providing information for correct placement of one or more brackets on one or more corresponding teeth according to a predetermined treatment scheme. A virtual representation of a three-dimensional teeth arrangement of one or both jaws of the individual with brackets placed on said teeth is obtained wherein the position and orientation of the brackets on said teeth being designed so as to achieve a desired treatment outcome. The virtual representation is processed to generate an output data, the output data driving a display, such as a computer monitor or a printed "hard-copy", to display an image of at least one tooth with a bracket thereon, the displayed image having three-dimensional qualities indicative of said at least one tooth as viewed from a defined viewpoint. The invention can be applied to the placement of brackets onto the buccal side of the teeth as well as onto the lingual side of the teeth.

11 Claims, 7 Drawing Sheets

U.S. PATENT DOCUMENTS

| | | | |
|---|---|---|---|
| 6,334,772 B1 | 1/2002 | Taub et al. | 433/24 |
| 6,334,853 B1 | 1/2002 | Kopelman et al. | |
| 6,350,120 B1 | 2/2002 | Sachdera et al. | 433/24 |
| 6,413,083 B1 | 7/2002 | Hamilton | 433/24 |
| 6,739,869 B1 | 5/2004 | Taub et al. | |
| 2002/0025503 A1 | 2/2002 | Chapoulaud et al. | 433/24 |
| 2002/0064759 A1* | 5/2002 | Durbin et al. | 433/213 |

FOREIGN PATENT DOCUMENTS

| | | |
|---|---|---|
| WO | WO 99/16380 | 4/1999 |
| WO | WO 99/34747 | 7/1999 |
| WO | WO 01/80761 A2 | 11/2001 |

OTHER PUBLICATIONS

Kopelman et al., U.S. Appl. No. 60/288,522, "A Method and System for Assessing the Outcome of an Orthodontic Treatment", filed May 3, 2001, 47 pages.

* cited by examiner

METHOD AND SYSTEM FOR ASSISTING IN APPLYING AN ORTHODONTIC TREATMENT

This is a Continuation Application of U.S. patent application 10/059,728 filed Jan. 29, 2002, now abandoned the contents of which are hereby incorporated by reference in its entirety.

FIELD OF THE INVENTION

The present invention is generally in the field of orthodontics. More specifically, the present invention relates to a computerized method and system for assisting an orthodontist in applying orthodontic treatment.

BACKGROUND OF THE INVENTION

Orthodontic treatment has the object of aligning and repositioning teeth for both functional and aesthetic purposes. This is achieved by the use of a variety of orthodontic appliances including, brackets, wires (arch wires), coil springs and elastics. In combination, these appliances are fixed to teeth in such a manner that orthodontic forces and moments cause the teeth to move in the desired direction.

There are currently acceptable guidelines in orthodontics which define the optimal dental and skeletal relations which should be the goal of orthodontic treatments. A summary of these guidelines can be found in *Straight Wire, the Concept and Appliances*, by Laurence F. Andrews, L. A. Well, Co., San Diego, Calif., USA, 1989. These guidelines are based on both functional and aesthetic considerations.

The outcome of orthodontic treatment is dependent, among others, upon the accuracy of the positioning of the orthodontic bracket. Brackets are selected and applied to the teeth in order to achieve the results indicated by the treatment plan. However, if the bracket is not precisely placed in its designated position, this will cause the tooth to move in a direction other than the one desired, with the result that the desired outcome cannot be obtained. Thus, there is a need in the art to provide orthodontists with a tool to assist in applying an orthodontic treatment according to a treatment plan designed accordingly, and specifically, to assist in precisely placing brackets in their respective positions as designated by the plan.

U.S. Pat. No. 6,334,772 in the name of the same applicant describes a method and system for placement of orthodontic appliances on teeth. In this patent, use is made of a small video camera mounted on a device that applies the bracket onto the tooth. By monitoring the view captured by the camera against an image of an intended bracket position, the correct position may be achieved.

GENERAL DESCRIPTION OF THE INVENTION

The present invention provides a method and system for providing information to assist in the correct placement of brackets on teeth. In accordance with the invention, an image is displayed on a screen, for example, a computer screen, which shows a segment of the teeth, including at least one tooth, with brackets placed thereon in a position in orientation in which the brackets are to be attached to the teeth to achieve the desired treatment result. The image of the teeth is segment displayed in this manner has three-dimensional ("3-D") qualities and resembles a view as viewed by the orthodontist from a defined viewpoint. This viewpoint is typically a preferred viewpoint and corresponds to that from which the teeth are viewed when a bracket is applied thereon. At times there may be a number of preferred viewpoints and in accordance with some embodiments of the invention, a set of images of the same teeth segment is displayed from two or more preferred viewpoints. This set of images may be displayed either simultaneously or sequentially. The term "three-dimensional qualities" should be understood as pertaining to the display of an image that has three-dimensional clues therein. For example, an image with 3-D qualities may be an image displayed on a two-dimensional screen with clues in the form of shading or a variety of other graphical means to give an impression as if the image is a 3-D image. It is possible, also, to make the display as a virtual 3-D display which can be viewed through the use of specific goggles (for example, 3-D information may be color coded and by the use of appropriate colored lenses, a 3-D virtual image is obtained).

In the following, the term "proper placement" will be used to denote the position and orientation of a bracket on a tooth which is designed (or believed) to achieve a desired treatment outcome. A desired treatment outcome is one that yields optimal dental and skeletal relationships acceptable in orthodontics. Thus, a proper placement refers to apposition and orientation of a bracket which will yield, within the framework of real-life treatment, a desired treatment outcome.

The basis for the displayed image is a virtual representation of a 3-D teeth arrangement with the brackets placed on the teeth. The virtual representation is an ensemble of digital data that can be stored in a computer readable medium and when read by the computer, typically aided by dedicated software, can be used to obtain spatial information on the teeth arrangement. It should, however, be noted that the virtual representation need not be presentable on a screen as such and it is at times sufficient for it to exist within the virtual environment of the computer in a manner that permits to generate output data that in turn drives the display of an is image of a segment of the tooth with a bracket placed thereon.

Said virtual representation can be obtained by acquiring data on a 3-D arrangement of the teeth, for example in the manner described in U.S. Pat. No. 6,334,853 in the name of the same applicant, and then processing the data by incorporating brackets and applying them virtually onto the teeth, in a manner that in a real-life treatment is regarded as proper placement to achieve a desired treatment outcome. A proper placement design may be made by a virtual orthodontic treatment carried out on a virtual 3-D teeth model, for example as described in U.S. applications Ser. Nos. 09/591,757 and 60/288,522 in the name of the same applicant, the content of which is incorporated hereby by reference. The purpose of such virtual treatment is to design the orthodontic treatment to achieve optimal results. For example, to achieve the goal of an orthodontic treatment according to the guidelines laid down in *Straight Wire, the Concept and Appliances*, by Laurence F. Andrews, L. A. Well, Co., San Diego, Calif., USA, 1989.

Alternatively, the virtual representation may be made by the orthodontist, through combining the 3-D data of the spatial teeth arrangement with brackets using computer aided design techniques. The orthodontist may in this manner virtually attach brackets to the teeth, determining the proper position based on his experience, and thus generate the virtual representation in this manner. As will be appreciated, the invention is not limited in any way to the manner in which the virtual representation of the teeth arrangement within the brackets is obtained.

The virtual representation after it is obtained is utilized to generate an output data which then drive the display to display an image of a segment of the teeth, with at least one tooth with the brackets placed thereon, which can then guide the proper placement of the bracket on the tooth.

According to one aspect the invention, there is thus provided a method for providing information for the correct placement of one or more brackets onto corresponding one or more teeth according to a predetermined treatment scheme, the method comprising:

obtaining a virtual representation of a three-dimensional teeth arrangement of one or both jaws of the individual with brackets placed on said teeth, the position and orientation of the brackets on said teeth being designed so as to achieve a desired treatment outcome; and processing said virtual representation to generate an output data, the output data driving a display to display an image of at least one tooth with a bracket thereon, the displayed image having three-dimensional qualities indicative of said at least one tooth as viewed from a defined viewpoint.

According to another aspect of the invention, there is provided a system for providing information for correct placement of one or more brackets on corresponding one or more teeth according to a predetermined treatment scheme, the system comprising:

a processor module for obtaining a viral representation of a three-dimensional teeth arrangement of one or both jaws of the individual with brackets placed on said teeth, the position and orientation of the brackets on said teeth being designed so as to achieve a desired treatment outcome and for processing said virtual representation to generate an output data the output data adapted to drive a display to display an image of at least one tooth with a bracket thereon, the displayed image having three-dimensional qualities indicative of said at least one tooth as viewed from a defined viewpoint; and a display linked to said processor module for displaying said image.

In accordance with another aspect, there is provided a system for providing information for the correct placement of one or more brackets on corresponding one or more teeth according to a predetermined treatment scheme, the system comprising:

a data input module for acquiring and storage of data representative of a three-dimensional teeth arrangement:

a processor and software running in said processor for processing said data, to obtain a virtual representation of a three-dimensional teeth arrangement of one or both jaws of an individual (placed on said teeth);

an image generation module coupled to or running within said processor for generating an output data adapted to drive a display to display an image of at least one tooth with a bracket thereon, the displayed image having three-dimensional qualities indicative of said at least one tooth as used from a defined viewpoint; and a display owing to said image generating module for displaying said image.

The term "predetermined treatment scheme" should be understood as meaning the combination of bracket positioning, the choice of arch wire as well as the choice of other orthodontic appliances to be used in an orthodontic treatment to achieve a desired outcome for orthodontic treatment.

In accordance with one preferred embodiment, the defined viewpoint is a preferred viewpoint which—corresponds to that from which the orthodontist views the at least one tooth viewed when applying brackets thereon within the framework of the real-life treatment. The display may provide two or more preferred viewpoints which may be provided all at the same time or in succession.

In accordance with another preferred embodiment, the output data is selected to drive the display to display a set of images of different teeth, either simultaneously or sequentially. For example, the different displayed teeth may be displayed in the same order in which the teeth are treated during the bracket placement procedure.

In accordance with one embodiment, the virtual representation data is transmitted from a remote location. For example, the orthodontic clinic may be connected to a central location which transmits to the clinic already the virtual representation which can then be applied immediately by the orthodontist at the clinic for implementing a treatment scheme decided upon in the central location. By another embodiment, the virtual representation is still generated by the system by combining the data that represents a three-dimensional arrangement of teeth with the data on proper bracket positioning.

The above mentioned embodiments can be applied to the placement of brackets onto the buccal side of the teeth (i.e. the traditional brackets called "labial brackets") as well as onto the lingual side of the teeth.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF SPECIFIC EMBODIMENTS

Figure 1:
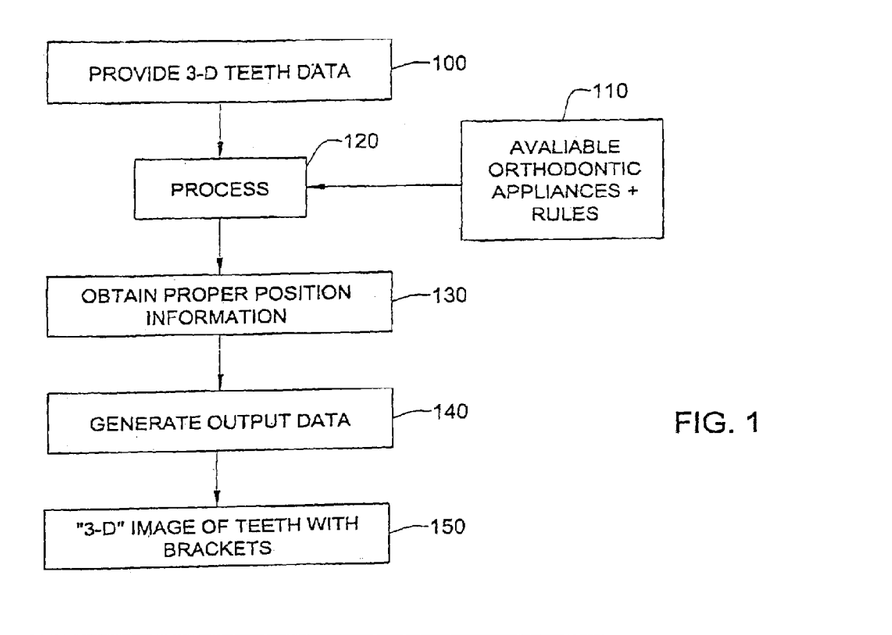
FIG. 1 shows a schematic flow diagram of the method according to an embodiment of the invention.

Reference is first being made to FIG. 1 showing, by way of a block diagram, a method in accordance with an embodiment of the invention. Data on a 3-D teeth arrangement of the patient 100 is obtained together with data 110 on available orthodontic appliances as well as on the rules to be applied in order to obtain a desired outcome. This information is then processed, for example by following the virtual orthodontic procedure as described U.S. applications Ser. Nos. 09/591,757 and 60/288,522, the contents of which is incorporated herein by reference, as well as generally outlined with reference to FIGS. 7A and 7B below. In this matter, the 3-D virtual representation of the teeth with brackets placed thereon, with the brackets having a position and orientation to achieve a desired treatment outcome is obtained at 130. From this representation, a series of output data 140 is obtained, each such output data defining a certain teeth segment including at least one tooth with a bracket placed thereon (with the bracket being properly positioned) from a defined viewpoint, in order to view a certain teeth segment from a variety of different viewpoints, corresponding to a number of output data generated. The output data 140 can then derive a display, in ways known, per se, to yield a 3-D image of teeth with brackets which can then guide the orthodontist for proper positioning of the brackets on the patient's teeth.

Figure 2:
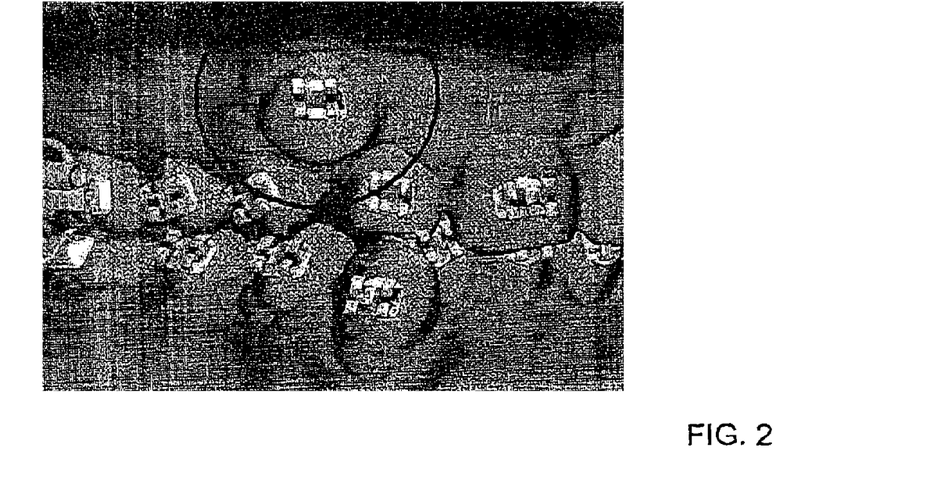
FIG. 2 shows a 3-D image section of a virtual representation of the teeth with brackets placed thereon, with the brackets positioned at the proper position to achieve a desired treatment outcome.

FIG. 2 shows an example of a 3-D representation of teeth with brackets which is the kind of data represented by block 130 in FIG. 1. As indicated above, this representation is presented herein in the form of an image but, as can be appreciated by the artisan, this 3-D representation does not need to be represented in the form of an image and it is at times sufficient for it to exist virtually within the virtual environment of the computer.

Figure 3:
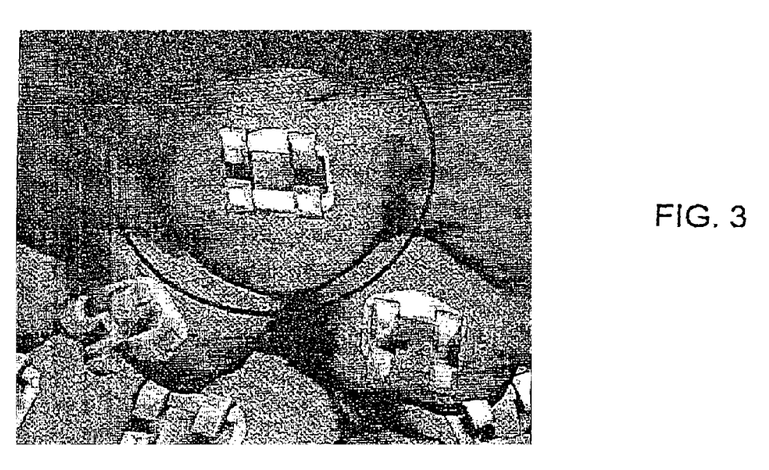
FIG. 3 shows an image of a segment of teeth, with one tooth centered (circled) at an undefined viewpoint.
Figure 4:
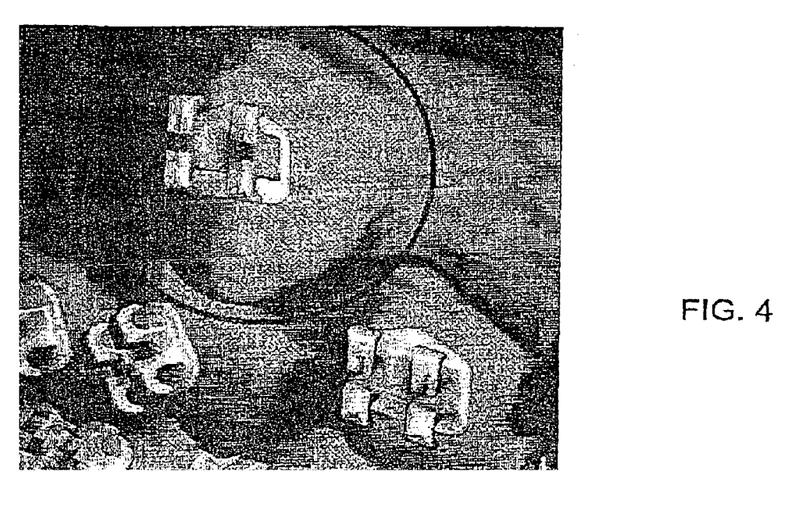
FIG. 4 shows the same tooth at another defined viewpoint.

FIG. 3 shows an example of a 3-D image of teeth with brackets as viewed from one defined viewpoint, as represented in FIG. 1 by block 150. FIG. 4 shows the same tooth from a different viewpoint. FIG. 3 shows a 3-D image as seen from a frontal viewpoint, while FIG. 4 is a viewpoint—as seen by the orthodontist when placing the bracket on the tooth.

Figure 5:
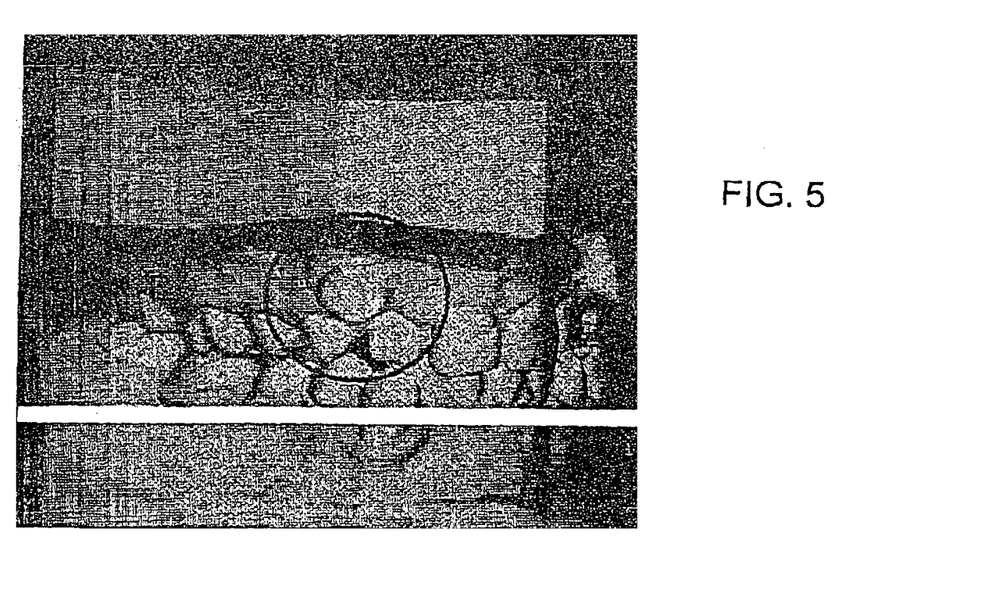
FIG. 5 shows a 3-D representation of a teeth arrangement of an individual prior to orthodontic treatment.
Figure 6:
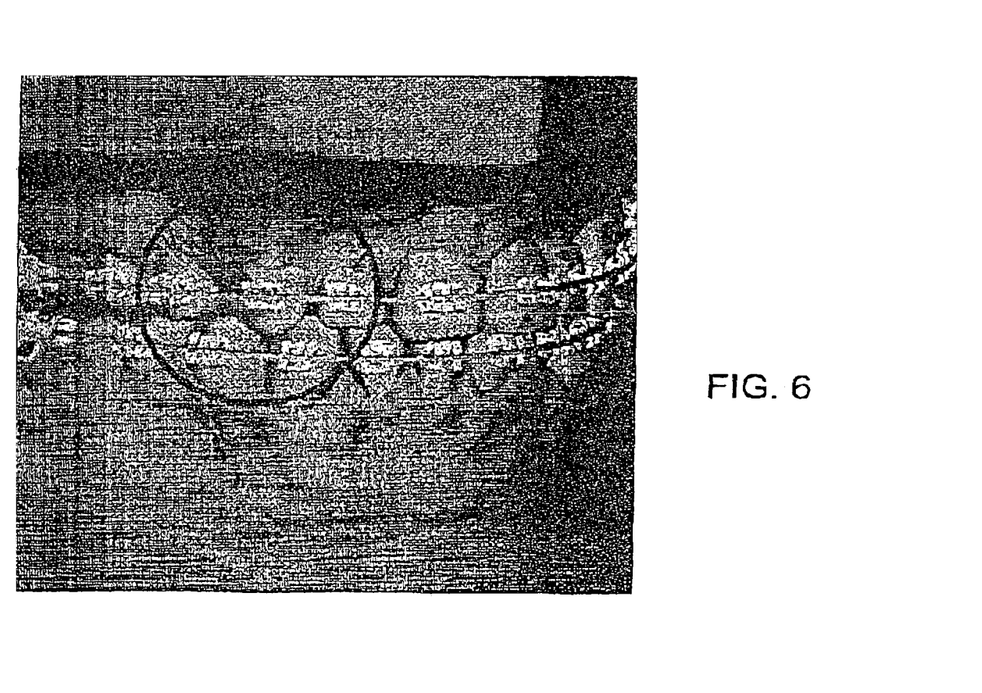
FIG. 6 shows the teeth of the same individual after the step of virtual orthodontic treatment showing the final outcome of the treatment (which in this case is a desired outcome of the treatment).

FIGS. 5 and 6 show images representing different stages of the process described in FIG. 1. FIG. 5 is a representation of the 3-D arrangement of teeth as inputted to the method (block 100 of FIG. 1) while FIG. 6 shows the same teeth after virtual treatment processes. By maintaining the brackets on the teeth and then allowing the teeth (in a virtual sense) to avert back to their original position as seen in FIG. 5, an image such as that shown in FIG. 2 and thereafter the 3-D image of FIGS. 3 and 4 can thus be obtained.

Figure 7A:
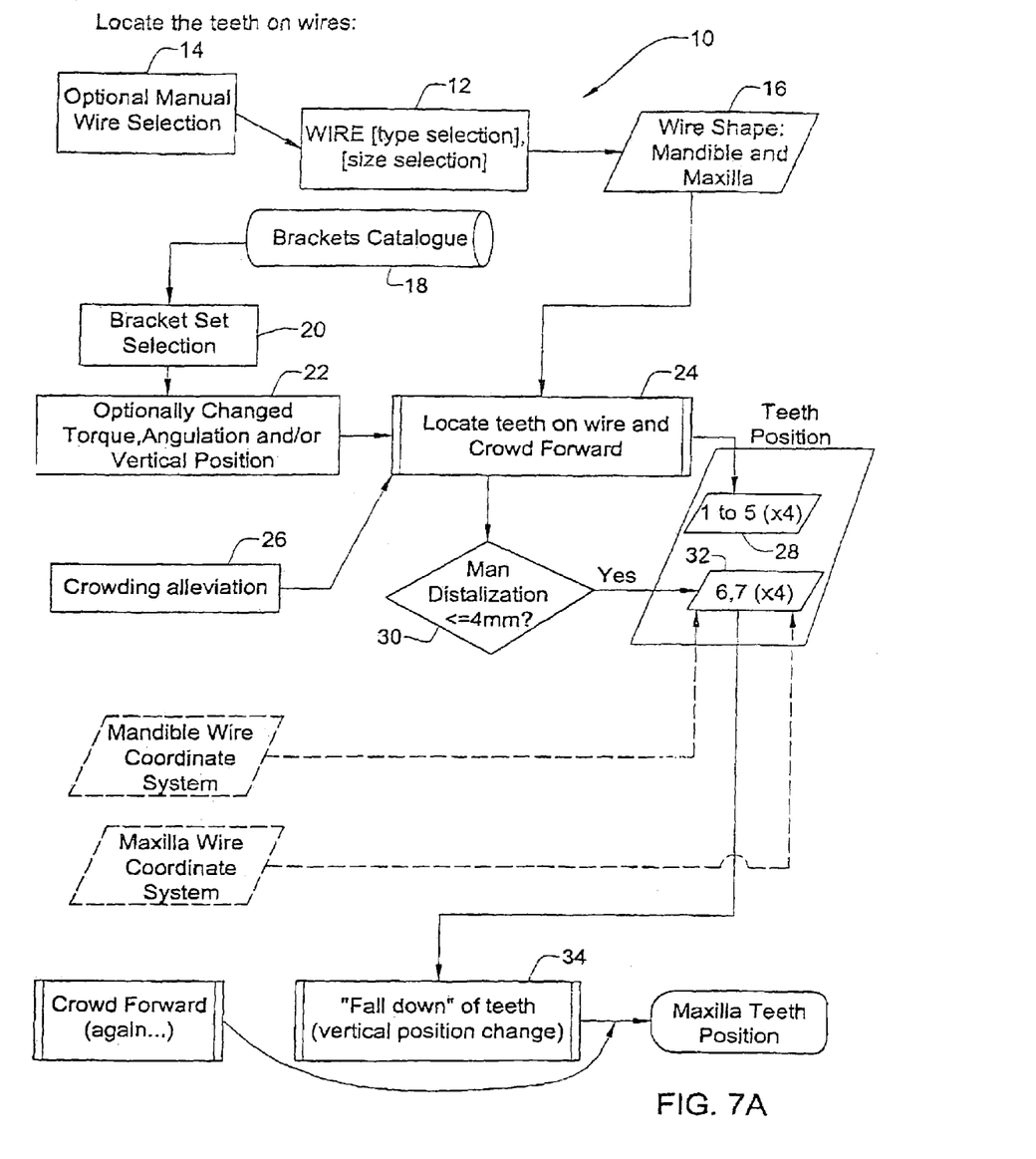
FIGS. 7A and 7B show a block diagram of the virtual orthodontic treatment.
Figure 7B:
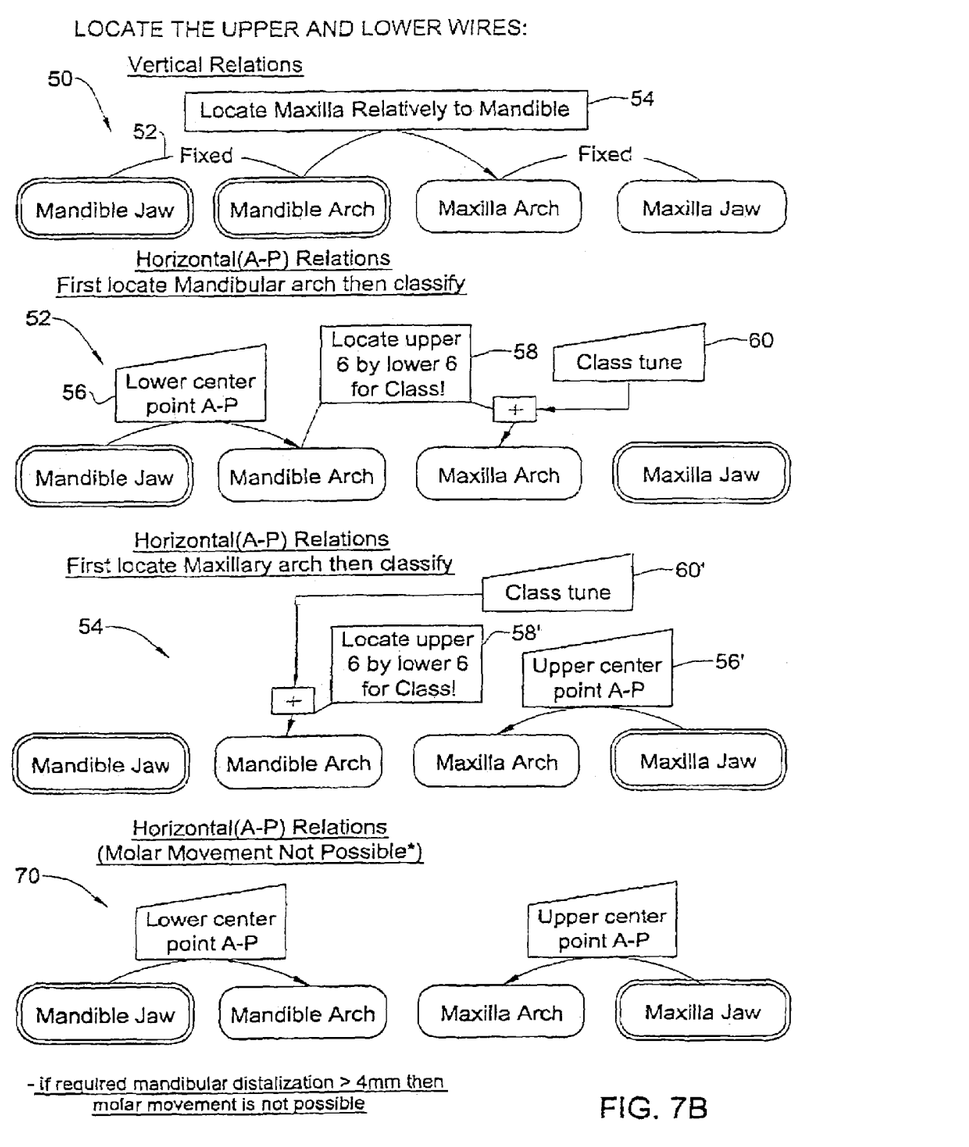

FIGS. 7A and 7B show, by way of a block diagram, a scheme of orthodontic treatment which can be used to generate the virtual representation of the teeth with the bracket (represented by block 120 in FIG. 1). For a more general description, reference is made to U.S. Application Ser. No. 60/288,522.

Reference is now made to FIG. 7A which shows a flow diagram 10 showing the manner in which teeth are positioned and fixed onto arch wires. According to diagram 10, the process begins with selecting the type of wire to be used in the virtual treatment. The selection of the wire (12) may either be achieved automatically by the system or selected by the user (14). The automatic selection is based in principal on minimal teeth movement in the jaw. A wire is selected for both the mandible and the maxilla (16). Typically, the wires for the mandible and maxilla are selected based on the profile, size etc., of the wire.

In addition, brackets are selected from brackets catalog 18. The brackets selected (20) may be further manipulated by changing their torque, angulations and/or vertical positioning on to the wire (22).

The outcome of the above procedure is an arch wire set with brackets which are fixed with the respective teeth, the teeth being optimally arranged according to orthodontic criteria (28). At times, movement of the first molar teeth by the system of the invention may result in a distilization of the mandibular molar teeth to (mandible distilization (30)) to a greater extent than that allowed in real life treatment according to real life treatment considerations. Accordingly, after the translation of teeth as described above, the system verifies whether the mandibular distilization performed would be allowed in real life considerations and if in the negative, the result displayed on the display screen will show the user that is the procedure performed would not be feasible in real life orthodontic treatment. The user will then know that the orthodontic treatment plan he selected should be changed, e.g. by selecting a different wire, different brackets, performing other, if any, manipulations on the teeth, etc.

The resulting arrangement of the teeth may further be processed by applying a vertical repositioning of the teeth (34), and it necessary, by further crowding the teeth as already performed (step (ii) above). The result obtained for one arch, i.e. the maxillary arch or the mandibular arch, is then used for the determination of the inter arch relationship.

Reference is now made to FIG. 7B which shows the steps for determining the inter arch relationship. In particular, FIG. 7B shows flow diagrams 50, 52, 54 and 70 describing the steps for obtaining vertical and horizontal alignments of the mandible and maxilla.

Flow diagram 50 describes vertical alignment of the mandible and the maxilla. Accordingly, the mandibular arch is first aligned with the mandibular jaw by their central point (an average distance between the central incisors) to fall onto the mid palatal plane (52). The maxillary arch fixed onto the maxillary jaw is then vertically aligned onto the mandibular jaw in the manner as described in U.S. Pat. No. 6,334,853, the contents of which is incorporated herein by reference (54).

Flow diagram 52 and 54 show the horizontal alignment between the maxilla and mandible. Flow diagram 52 shows alignment of the maxilla according to fixed mandible parameters, while flow diagram 54 shows the alignment of the mandible according to the maxilla.

The following description refers to alignment of the maxilla according to the fixed mandibular. However, it should be understood that the same steps apply in flow diagram 54, for alignment of the mandible according to the fixed maxilla jaw (mualis mutandis).

For determining the inter arch relationship, first the parameters of the mandibular jaw are provided, with which the mandibular arch is aligned by determining their center antheroposterior point (lower center point A-P (56). Then, is occlusion of the mandibular first molar with the maxillary first molar is dictated by the features of Class (I) type of occlusion (58). If necessary, i.e. when the outcome obtained and displayed on the display screen is not the desired outcome or when the user decides it is required to change the Class type, he may change the class by which the mandibular first molar and the maxillary first molar interlock, until reaching the desired outcome (60).

At times, the horizontal alignment performed will result in a mandibular distilization which is greater than that acceptable in real life orthodontic treatment. As a result, the procedure according to the invention is carried out according to flow diagram 70. This flow diagram shows that when desired or required, while each arch is positioned onto their respective jaw by defining their center antheroposterior point, the steps of interlocking the molar teeth according to standard orthodontic guidelines is not performed.

Figure 8:
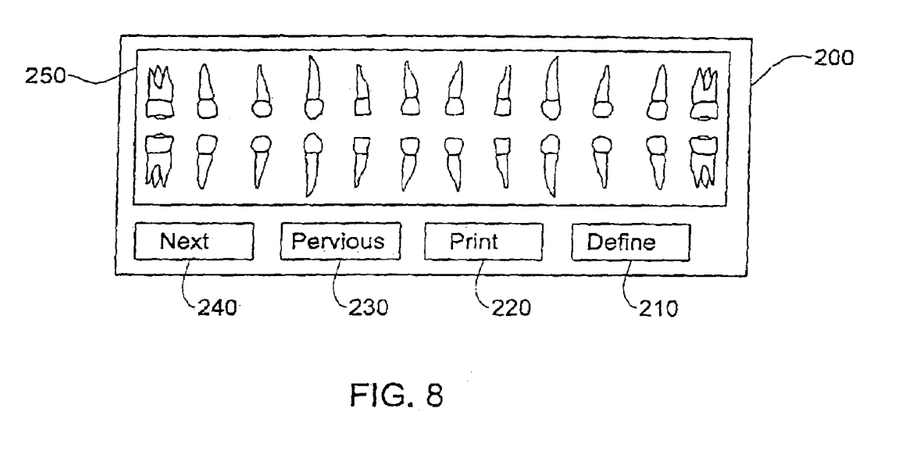
FIG. 8 shows an interface that permits the orthodontist to select the teeth to be imaged on the display.

The user is provided with a graphic user interface window such as window 200 of FIG. 8, on a display such as a computer screen. The graphic user interface. window 200 displays 'DEFINE' option 210, which enables the user to define the tool's operational characteristics, shown in FIG. 9 as step 300. In step 300, the user is able to select the order in which the images of the different teeth will appear, according to his personal preference and professional practice. The user will be able to select among several optional sequences such as: (1) upper jaw first, from left side to the right; (2) upper jaw first, from the middle to the right and then from the middle to the left, and so on. The user also will be able to select the view from which the visual data will be displayed. Typically, the user will be offered to select frontal viewpoint or a viewpoint from the side of the viewpoint as seen by the orthodontist when placing the bracket on the tooth. According to the last-mentioned option, different teeth will be viewed from different angles with respect to a fixed reference line. The user is also able to select an option to view the designated position of the bracket from a presentation from one viewpoint followed by a presentation of the same tooth from another view. The user might also choose to view simultaneously both images by utilizing split Windows (not shown). Additionally, the user will be able to select views from additional angles.

Figure 9:
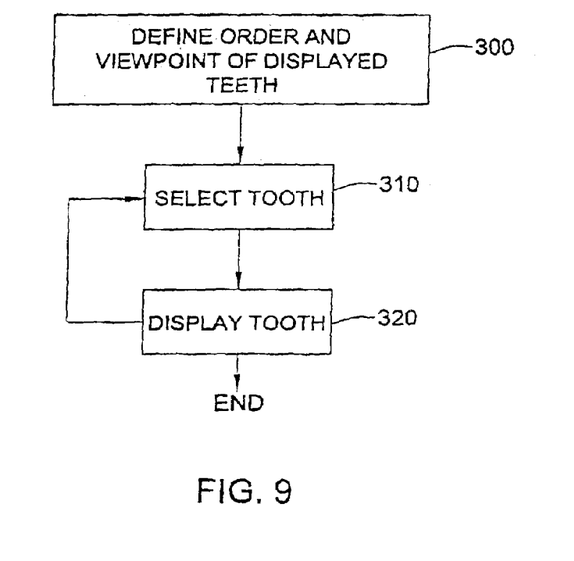
FIG. 9 is a block diagram explaining the manner of utilizing the system of the invention.

The user might carry out step 300 only once, as a preset step, or may choose to redefine the operation characteristics on each operation of the tool. Nevertheless, the operational characteristics of the tool can be predefined without offering the user the possibility of personal customization.

Back to FIGS. 8 and 9: At step 310, the user selects a tooth, typically by pushing the 'NEXT' button 240 or by marking a specific tooth from teeth display 250. Then at step 320, the user is provided with an image of the selected teeth as shown in FIGS. 3-4. Upon turning to the next tooth, the user repeats steps 310 and 320 and the image of the next tooth is presented according to the preset order defined at step 300, until the last tooth is viewed. At any time the user can manually change the order of the viewed teeth, by selecting 'NEXT' button 240, 'PREVIOUS' button 230 or by using teeth display 250 of FIG. 8. Also shown in FIG. 8 is the 'PRINT' button 220, which enables the user to print a set of images as shown in FIGS. 34 from different views and in a desired order, as described above. (The 'PRINT' option obviously requires the system to be connected to a printer).

The above mentioned embodiments can be applied to the placement of brackets onto the buccal side of the teeth (i.e. the traditional brackets called "labial brackets") as well as onto the lingual side of the teeth.

Figure 10:
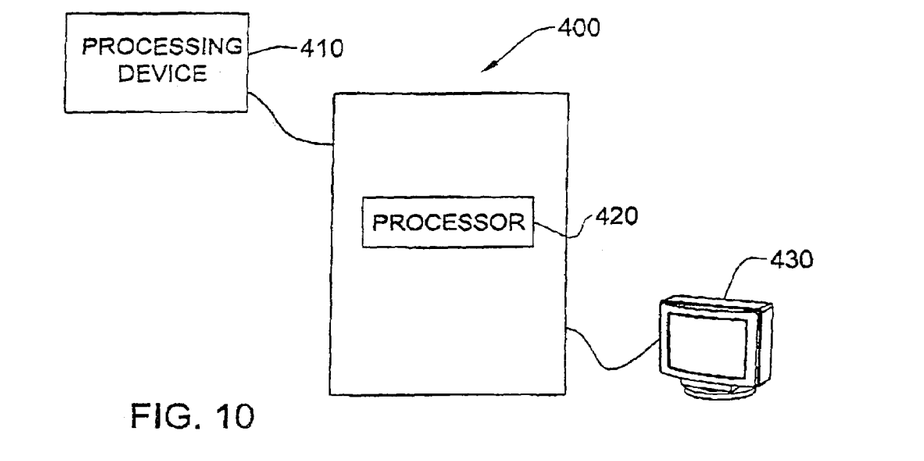
FIGS. 10 and 11 show two embodiments of systems in accordance with the invention.

FIG. 10 show a system 400 in accordance with one embodiment of the invention, for providing information for the correct placement of one or more brackets on corresponding one or more teeth according to a predetermined treatment scheme. System 400 is connectable to a processing device 410 (which is not a part of the invention) to provide 3-D teeth data. System 400 comprises a processor module 420 for obtaining a virtual representation of a three-dimensional teeth arrangement of one or both jaws of the individual with brackets placed on said teeth, the position and orientation of the brackets on said teeth being designed so as to achieve a desired treatment outcome and for processing said virtual representation to generate output data, the output data adapted to drive a display to display an image of at least one tooth with a bracket thereon, the displayed image having three-dimensional qualities indicative of said at least one tooth as viewed from a defined viewpoint. System 400 also comprises a display 430 linked to said processor module for displaying said image.

Figure 11:
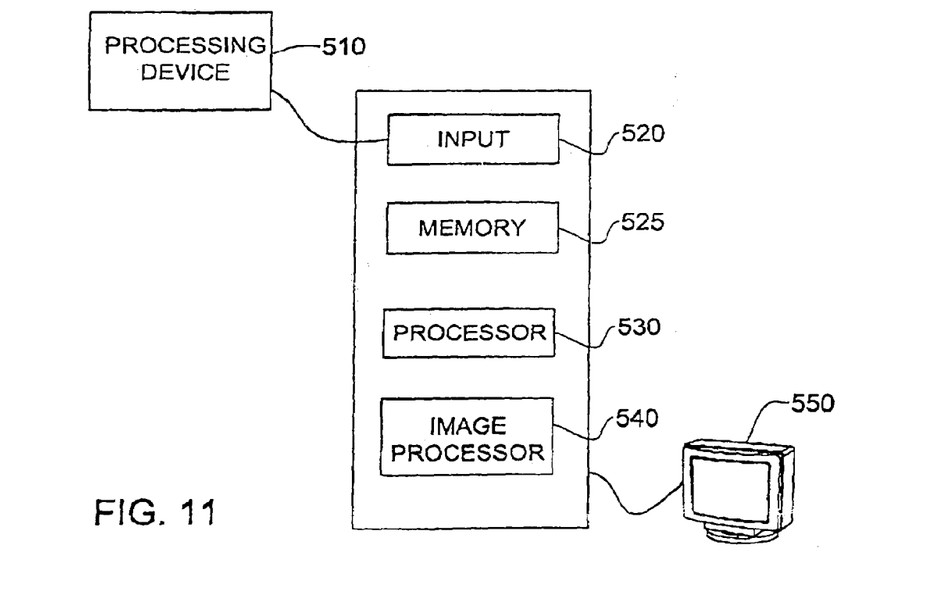

FIG. 11 shows a system 500 in accordance with another embodiment of the invention, for providing information for correct placement of one or more brackets on one or more corresponding teeth according to a predetermined treatment scheme. System 500 is connected to a processing device 510 and comprises a data input module 520 for acquiring and storing data representative of a three-dimensional teeth arrangement. System 500 also comprises a processor and software running in said processor 530, coupled to module 520 for processing said data, and memory 525 for storing a database of virtual brackets from which said software can import brackets for combining with the teeth, to obtain a virtual representation of a three-dimensional teeth arrangement of one or both jaws of an individual (placed on said teeth). An image generation module 540 coupled to or running within said processor for generating an output data adapted to drive a display to display an image of at least one tooth with a bracket thereon, the displayed image having three-dimensional qualities indicative of said at least one tooth as used from a defined viewpoint, and connectable to a display 550 linked to said image generating module for displaying said image. The systems 400 and 500 are also connectable to a printer (not shown), and thus can provide the user with a set of printed images according to the invention ("hard copy") to assist in placing the brackets in their proper position.

The invention claimed is:

1. A method for facilitating the correct placement of one or more brackets on corresponding one or more teeth according to a predetermined treatment scheme, the method comprising:

obtaining a virtual representation of a three-dimensional teeth arrangement of one or both jaws of the individual with brackets placed on said teeth, the position and orientation of the brackets on said teeth in the virtual representation, being designed so as to achieve a desired treatment outcome;

processing said virtual representation to generate an output data, the output data driving a display to display a virtual image of at least one tooth with a bracket thereon, the displayed image having three-dimensional qualities indicative of said at least one tooth as viewed from a defined viewpoint, wherein said three dimensional representation is suitably coded so that said displayed image appears as a three dimensional virtual image when said displayed image is viewed via a suitable optical arrangement; and while placing said one or more brackets directly on corresponding said one or more teeth of said individual, using said displayed virtual image as a visual comparison guide to assist in proper positioning of said one or more brackets directly on corresponding said one or more teeth of said individual, wherein said three dimensional representation is color-coded, and said optical arrangement comprises suitably colored lenses.

2. The method of claim 1, wherein the defined viewpoint is a preferred viewpoint, being a viewpoint corresponding to that from which the at least one tooth is viewed when applying a bracket thereon.

3. The method of claim 1, wherein the output data drives the display to display a set of images of the at least one tooth from two or more preferred viewpoints.

4. The method of claim 1, wherein the output data drives the display to display a set of images of different teeth.

5. The method of claim 4, wherein the different displayed teeth are displayed in an order in which the teeth are attended to during bracket placement procedure.

6. The method according to claim 1, wherein said display is a computer monitor.

7. The method according to claim 1, wherein said display is a printer.

8. The method of claim 1, wherein the obtaining of a virtual representation comprises transmitting said representation from a remote location.

9. The method of claim 1, wherein the obtaining of a virtual representation comprises receiving data representative of three-dimensional arrangement of teeth of at least one jaw and processing said data to define position and orientation of brackets on the teeth to achieve a desired treatment outcome.

10. The method of claim 9, wherein the data representative of a three-dimensional arrangement of teeth of at least one jaw is received from a remote location.

11. A method for facilitating the correct placement of one or more real brackets on corresponding one or more teeth according to a predetermined treatment scheme, the method comprising:

selecting one or more virtual brackets corresponding to the one or more real brackets from a virtual bracket catalogue containing a plurality of virtual brackets     obtaining a virtual representation of a three-dimensional teeth arrangement of one or both jaws of the individual with virtual brackets placed on said teeth, the position and orientation of the virtual brackets on said teeth in the virtual representation, being designed so as to achieve a desired treatment outcome;

processing said virtual representation to generate an output data, the output data driving a display to display a virtual image of at least one tooth with a virtual bracket thereon, the displayed virtual image having three-dimensional qualities indicative of said at least one tooth as viewed from a defined viewpoint, wherein said three dimensional representation is suitably coded so that said displayed image appears as a three dimensional virtual image when said displayed image is viewed via a suitable optical arrangement;

while placing the one or more real brackets directly on corresponding one or more teeth of said individual, using said displayed virtual image as a visual comparison guide to assist in proper positioning of the one or more real brackets directly on corresponding said one or more teeth of said individual,     wherein said three dimensional representation is color-coded, and said optical arrangement comprises suitably colored lenses.

\* \* \* \* \*